(12) United States Patent
Kreatsoulas et al.

(10) Patent No.: US 11,351,352 B1
(45) Date of Patent: Jun. 7, 2022

(54) TAMPER RESISTANT CATHETER DEVICE

(71) Applicants: Nicholas C. Kreatsoulas, Poland, OH (US); Joseph Spalding, Elyria, OH (US); Michael Tracz, Brecksville, OH (US)

(72) Inventors: Nicholas C. Kreatsoulas, Poland, OH (US); Joseph Spalding, Elyria, OH (US); Michael Tracz, Brecksville, OH (US)

(73) Assignee: DAK Scientific, Inc., Poland, OH (US)

( * ) Notice: Subject to any disclaimer, the term of this patent is extended or adjusted under 35 U.S.C. 154(b) by 135 days.

(21) Appl. No.: 15/967,420

(22) Filed: Apr. 30, 2018

Related U.S. Application Data (60) Provisional application No. 62/491,490, filed on Apr. 28, 2017.

(51) Int. Cl.
*A61M 39/20* (2006.01)
*A61M 25/00* (2006.01)
(Continued)

(52) U.S. Cl.
CPC ........ *A61M 39/20* (2013.01); *A61M 25/0097* (2013.01); *A61M 25/02* (2013.01);
(Continued)

(58) Field of Classification Search
CPC ........... A61M 5/5086; A61M 39/1011; A61M 25/02; A61M 2039/0288; A61M 2025/0266; A61M 39/20; A61M 25/0097; A61M 2039/1038; A61M 2025/028; A61M 2039/0282; A61M 2205/0205; A61M 2205/0238; A61M 2209/04; A61M 5/50; A61M 2025/0098; A61M 2025/0246; A61M 2025/0253; A61M 2039/087; A61M 2039/1016; A61M 2039/1061; A61M 2205/276
See application file for complete search history.

(56) References Cited

U.S. PATENT DOCUMENTS

| | | | | |
|---|---|---|---|---|
| 4,213,456 A | * | 7/1980 | Bottger | A61M 5/31511 600/576 |
| 6,029,834 A | * | 2/2000 | Sanner | B65D 50/041 215/215 |

(Continued)

*Primary Examiner* — Amber R Stiles
*Assistant Examiner* — Avery Smale (57) ABSTRACT

A tamper resistant catheter device preventing unauthorized access, while permitting authorized intravenous medications through an inlet port. The device comprises a catheter line retainer having a base supporting the catheter line, a lumen adaptor engaged with the catheter line, and a locking clamp for clamping the catheter line within the catheter line retainer. An installation tool is provided having a breakaway handle and a locking cap for covering the lumen adaptor. Finally, a slotted retaining sleeve is installed using the breakaway handle of the installation tool for engagement with the locking cap and around the lumen adaptor. The slotted retaining sleeve engages the locking clamp to block removal of the locking clamp from the line retainer. Once the slotted retaining sleeve and locking cap are installed, the breakaway handle is removed. A removal tool disengages the locking cap from the slotted retaining sleeve for authorized access.

14 Claims, 7 Drawing Sheets

(51) Int. Cl.
*A61M 39/10* (2006.01)
*A61M 25/02* (2006.01)
*A61M 39/02* (2006.01)

(52) U.S. Cl.
CPC ... *A61M 39/1011* (2013.01); *A61M 2025/028* (2013.01); *A61M 2025/0266* (2013.01); *A61M 2039/0282* (2013.01); *A61M 2039/0288* (2013.01); *A61M 2039/1038* (2013.01); *A61M 2205/0205* (2013.01); *A61M 2205/0238* (2013.01); *A61M 2209/04* (2013.01)

(56) References Cited

U.S. PATENT DOCUMENTS

| | | | |
|---|---|---|---|
| 6,082,564 A * | 7/2000 | Trout | B65D 50/068 215/207 |
| 6,428,515 B1 * | 8/2002 | Bierman | A61M 25/02 128/DIG. 26 |
| 6,491,664 B2 * | 12/2002 | Bierman | A61M 25/02 128/DIG. 26 |
| D609,338 S | 2/2010 | Dozier, Jr. | |
| 8,434,421 B2 * | 5/2013 | Fagan | G09F 11/23 116/308 |
| 8,858,505 B1 | 10/2014 | Justus et al. | |
| 8,961,491 B2 | 2/2015 | Uber, III et al. | |
| 9,275,536 B2 | 3/2016 | Wetherill et al. | |
| 9,517,330 B2 * | 12/2016 | Witt | A61M 39/1011 |
| 2002/0156430 A1 * | 10/2002 | Haarala | A61M 25/0075 604/247 |
| 2003/0153865 A1 * | 8/2003 | Connell | A61M 1/285 604/28 |
| 2004/0158209 A1 | 8/2004 | Wright | |
| 2006/0247577 A1 * | 11/2006 | Wright | A61M 5/158 604/174 |
| 2007/0142784 A1 * | 6/2007 | Dikeman | A61M 25/02 604/174 |
| 2008/0097405 A1 | 4/2008 | Miller | |
| 2012/0151975 A1 * | 6/2012 | Kottenstette | B65D 55/14 70/167 |
| 2012/0312840 A1 * | 12/2012 | Hasegawa | A61M 31/00 222/215 |
| 2013/0144258 A1 * | 6/2013 | Ziebol | A61L 29/16 604/506 |
| 2014/0114240 A1 * | 4/2014 | Joedicke | A61M 5/2448 604/92 |
| 2016/0030285 A1 * | 2/2016 | Miceli | A61J 1/1437 215/207 |
| 2017/0043130 A1 | 2/2017 | Jones et al. | |
| 2017/0165437 A1 | 6/2017 | Lopansri et al. | |
| 2017/0326349 A1 | 11/2017 | Pagano, II et al. | |

* cited by examiner

TAMPER RESISTANT CATHETER DEVICE

CROSS-REFERENCE TO RELATED APPLICATIONS

This application claims priority from U.S. Provisional Application Ser. No. 62/491,490 filed Apr. 28, 2017, which is incorporated herein by reference.

FIELD OF INVENTION

The application relates to catheters having a locking mechanism for limiting access to catheter lines, and specifically to peripherally inserted central catheter (PICC) lines, or any common central line or tubing, with locking technology to prevent unauthorized access to inlets or injection ports.

BACKGROUND

As the number of intravenous (IV) drug abusers in the United States continues to increase, the number of drug addicted patients suffering from serious health concerns is also increasing. Abusers of IV drugs such as opioids like heroin often suffer from serious infections, or may require treatment by IV antibiotics and other medications during recovery from surgeries. Longer-term treatment with IV medications is typically accomplished by placing a peripherally inserted central catheter (PICC) line into the patient's venous system during a hospital stay. Once the PICC line is installed by a health care provider, further repeated injections of necessary medications can be easily and quickly accomplished using the PICC line and without the difficulty of finding a vein. After the patient is sufficiently recovered and discharged from the hospital with the PICC line still installed, such repeated medication injections are typically made by health care providers during less expensive outpatient or home care visits.

Unfortunately, providing unsupervised access to the PICC line after discharge enables IV drug abusing patients to inject illegal drugs or other substances using the PICC line, and results in increased risk of illegal drug overdoses and death. In order to enable the discharge of drug abusing patients from the hospital with a PICC line, an improved PICC line, or other catheter, with locking capabilities to prevent unauthorized access to injection ports is needed. One such device that locks a conventional PICC line port within a lidded box is described in U.S. Pat. No. 8,858,505. However, such a device is awkward and inconvenient for a patient to wear, and still further innovations are needed.

SUMMARY

A tamper resistant catheter device is provided for resisting unauthorized intravenous administration of substances to a patient via a common central line or tubing, such as a peripherally inserted central catheter (PICC) line into the patient's venous system. The device is configured for use with a catheter line having an inlet port in communication with the patient's venous system, but may also be used with a feeding tube or other central line providing an access port. The inlet port of the catheter line is supported within the device, including a line retainer component having a base supporting the catheter line, an internally threaded lumen adaptor end adjacent the inlet port of the catheter line, and a line retainer end for securing the catheter line adjacent the location of engagement with the patient's skin. The catheter line and inlet port are configured to be trapped and clamped within the line retainer component by a line clamp component, which is hinged (or otherwise secured) to the base for mating engagement to trap, cover and clamp the catheter line within the base when the line clamp component is closed. As the catheter line is generally a thin, flexible, plastic tube, an internal portion of the line clamp component includes stops extending outwardly from the line clamp. The stops engage and clamp the catheter line within the base to prevent leakage or blood flow through the line when the line clamp component is engaged with the base in a closed position. In the open position, a health care provider is able to administer authorized medications to the patient through the catheter line via the lumen adaptor end of the line retainer component. The lumen adaptor end of the line retainer component may be configured for any suitable fitting. The line retainer component may be secured to the patient using an adhesive pad having a line retainer mount.

Following administration of any authorized medications, the device may be locked to prevent unauthorized access to the catheter line. To secure and maintain the line retainer component in a closed and locked condition, a threaded locking cap and slotted locking or retaining sleeve are provided, along with a removal tool. The threaded locking cap, for threaded engagement with the lumen or lumen adaptor component includes a removable installation tool or handle portion. It should be understood that the internal configuration of the locking cap may be provided with internal threads for mating interconnection with the either a male or female Luer lock or taper connection configured in the lumen adaptor end of the line retainer component.

An annular skirt forming the cup-shaped locking cap is configured with spaced lugs extending from the skirt for locking engagement with interfitting locking surfaces provided on an inner annular surface of the slotted retaining sleeve. The slotted retaining sleeve is configured to be engaged over the lumen or lumen adaptor component, with the slot of the retaining sleeve engaging the housing to block access to the inlet port of the catheter line. Once the retaining sleeve is engaged surrounding the housing, the installation tool is used to rotate the locking cap and retaining sleeve into threaded and locking engagement with the lumen adaptor component. The installation tool portion may be snapped off for disposal once the cap and sleeve are locked in position.

To remove the locking cap and slotted retaining or locking sleeve, the device removal tool is used. The removal tool includes a finger surface for rotating the tool, and an annular skirt having spaced grooves for engagement with the spaced lugs formed on the locking cap. When the removal tool grooves are aligned with the locking cap lugs, the removal tool is slidably inserted between the threaded cap and the slotted retaining sleeve, and rotated using the finger surface, to disengage the interfitting locking surfaces from the spaced lugs of the locking cap, and unthread the locking cap from the lumen or lumen adaptor component. Thereafter the locking cap is removed with the removal tool, the retaining sleeve may also be removed, and the catheter line accessed by authorized health care providers.

A tamper resistant catheter device has been broadly described so that the more detailed description may be better understood. There are additional aspects of the device that will be described below, and it is understood that more than one embodiment of the device is provided. The device is capable of still further implementations in addition to those described. It is understood that the terminology used is provided to describe the device, and should not be regarded as limiting, as those of ordinary skill in the art will readily understand the basis set forth here by which other equivalent structures, methods and systems may be provided which do not depart from the spirit and scope of this tamper resistant catheter device.

DESCRIPTION OF THE DRAWINGS

FIGS. 24 to 28 schematically illustrate side views of the installation of an alternate embodiment of a threaded cap and retaining sleeve forming a tamper resistant catheter device used with an Arrow® brand PICC line lumen:

FIGS. 29 to 33 schematically illustrate side views of the steps for removal of the threaded cap and retaining sleeve from the PICC line shown in FIG. 28:

DETAILED DESCRIPTION

Figure 1:
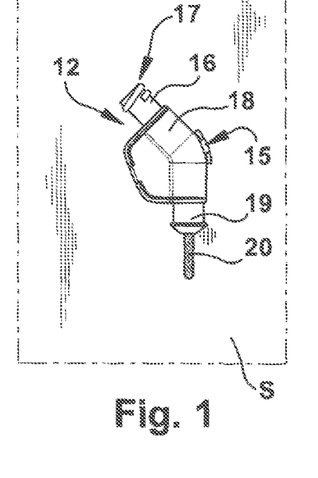
FIG. 1 is a top plan view of the line retainer and clamp, or housing, of the tamper resistant catheter device of this application showing a PICC line mounted on and in a patient, and secured within a housing, shown in a closed position, for clamping the PICC line and preventing leakage.

A tamper resistant catheter device 10 or PICC line lock is provided to prevent unauthorized access to a catheter line having an inlet port in communication with the patient's venous system. The patient is provided with a catheter or PICC line 20 by a health care provider in a medical facility. The line is supported within a housing 12 (in an unclamped or open position) to allow the physician's installation guide wire to pass through the housing. Once the guide wire is removed, the housing is quickly closed to clamp the line 20, see FIG. 14, and prevent leakage, as in FIG. 1.

The device 10 includes the housing 12 having a line retainer or base 14, a lumen adaptor component 16, and a line clamp portion 18. Additionally, the device includes a locking cap 30, a slotted retaining sleeve 40 and a removal tool 50. The inlet port 22 of the catheter line 20 is supported within the line retainer or base 14, as shown in FIG. 4. The lumen adaptor 16 includes a threaded lumen adaptor end 17 adjacent the inlet port 22 of the catheter line, and a line retainer end 19 for securing the catheter line 20 adjacent the location of engagement with the patient's skin S. The catheter line 20 and inlet port 22 are configured to be trapped and clamped within a groove 13 formed by the line retainer 19 and the line clamp portion 18, which is hinged (or otherwise secured) at an interconnection or hinge joint 15 to the base 14 to trap, cover and clamp the catheter line within the groove when the line clamp portion 18 is closed. Any conventional snap closure, such as a mating boss and groove engagement, may be used to secure the hinged line clamp portion 18 closed. As the catheter line 20 is a thin, plastic tube, an internal portion of the line clamp portion includes stops or stop surfaces 60 extending from the groove 13 outwardly from the line clamp portion 18, as shown in FIGS. 4 and 5. The stops or stop surfaces 60 engage and clamp the catheter line 20 within the base 14 to prevent leakage or blood flow through the line when the line clamp portion 18 is engaged with the base in a closed position, as in FIGS. 1 to 3. Blood B may be seen in FIGS. 1 to 3 within the line 20 between the skin and the line retainer end 19 of the base 14.

Figure 6:
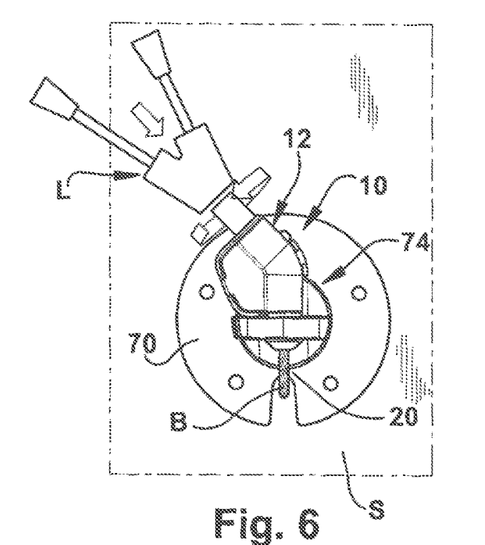
FIG. 6 is a schematic top plan view of the PICC line housing of FIG. 3, and with a lumen attachment with dual ports schematically showing the connection of the lumen attachment to a lumen adaptor component of the housing.
Figure 7:
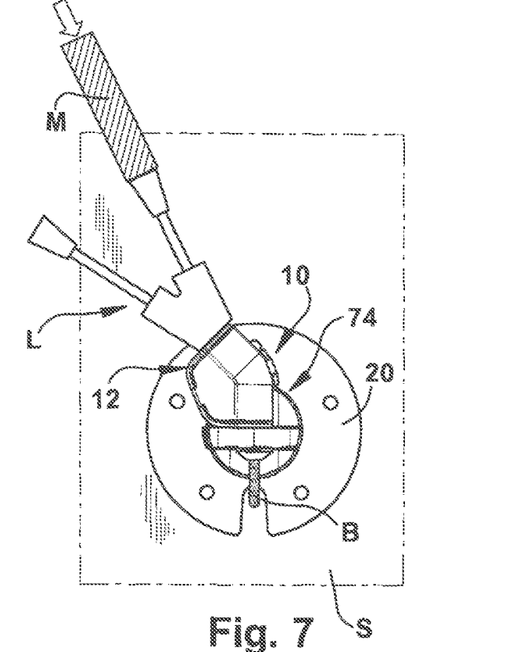
FIG. 7 is a schematic top plan view showing a medication container or vial interconnected with one port of the lumen attachment.
Figure 8:
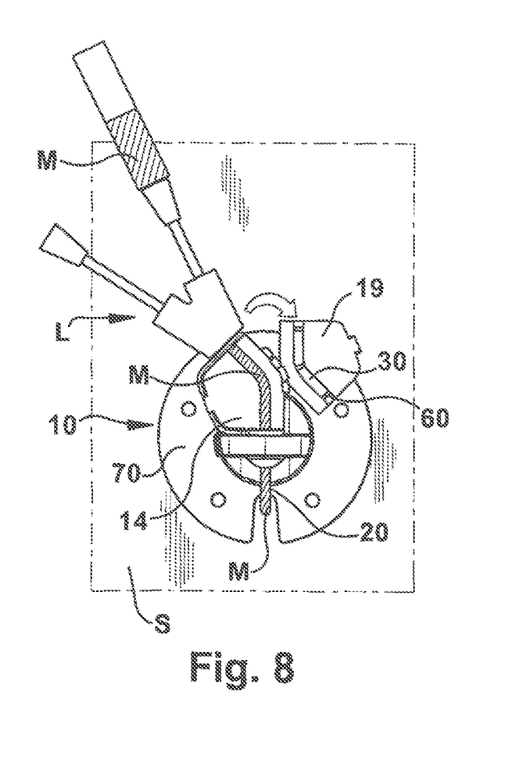
FIG. 8 is a top plan view schematically showing the medication within the medication container being injected through the PICC line and an open housing, which unclamps the PICC line in the open position.
Figure 9:
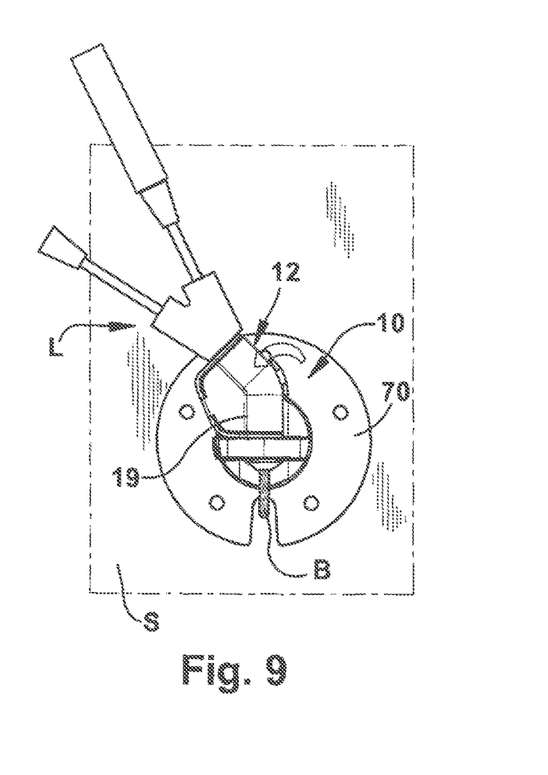
FIG. 9 is a top plan view schematically showing the closing of the housing to again clamp the PICC line, once the medication within the medication container has been dispensed, and is ready to be removed from the lumen attachment.
Figures 10A, 10B, 10C, 10D, 11A, 11B, 11C, 12A, 12B, 12C, 12D, 13, 14A, 14B:
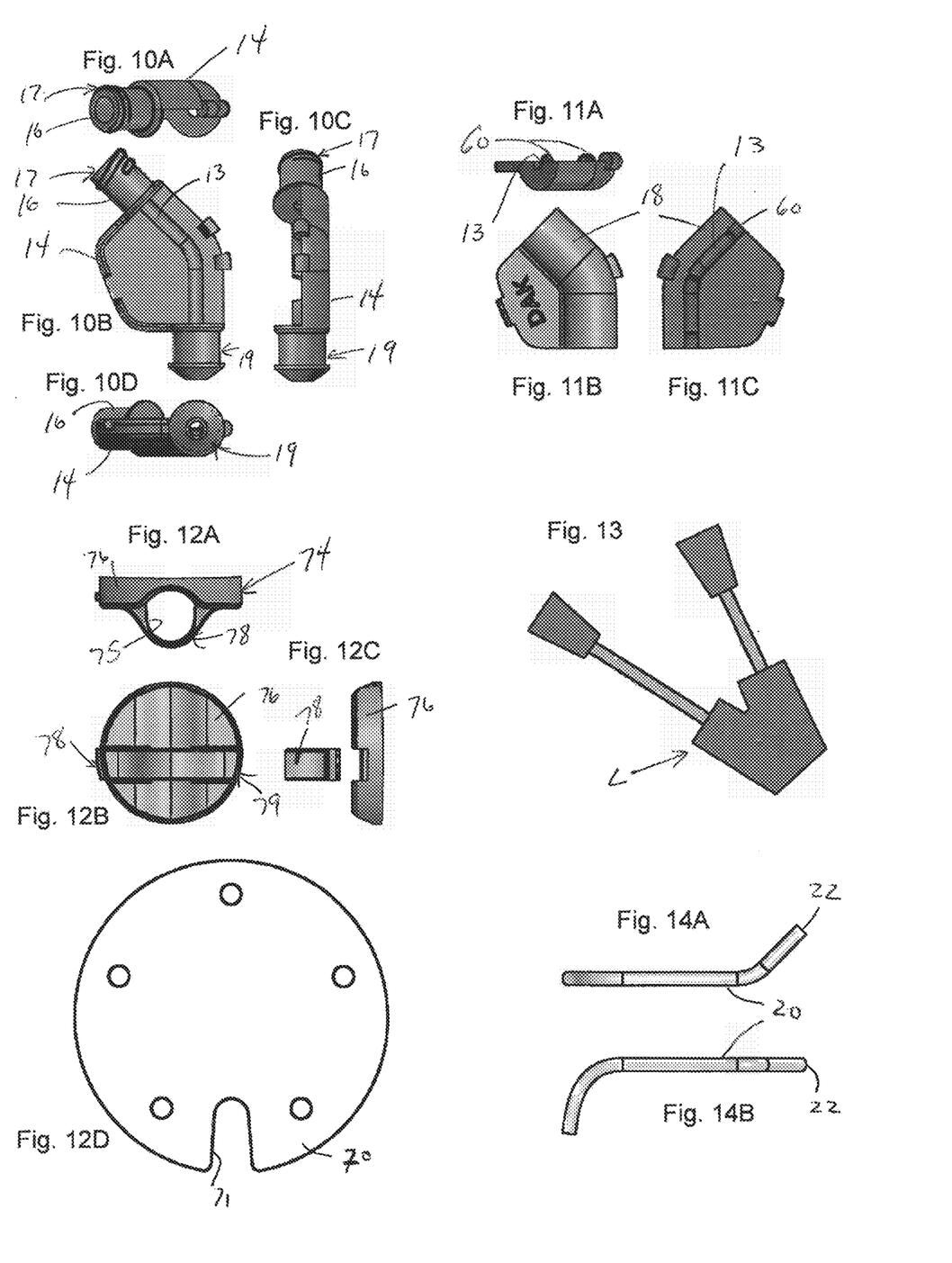
FIGS. 10A to 10D schematically show a base or line retainer portion of the PICC line housing, including a lumen adaptor end view in 10A, a top plan view in 10B, a side view in 10C, and a line retainer end view in 10D.
FIGS. 11A to 11C schematically show a line clamp portion of the PICC line housing removed from hinged engagement with the base or line retainer portion, including a top end view in 11A, a top plan view in 11B, and an inner or bottom plan view in 11C.
FIGS. 12A to 12D schematically show an adhesive pad and mount for the base or line retainer portion of the PICC line housing, including a top end view of the mount in 12A, a top plan view of the mount in FIG. 12B, an exploded side view of the mount with the hinged clamp portion shown removed from the mount portion in 12C, and a top plan view of the adhesive pad supporting the PICC line housing in 12D.
FIG. 13 schematically illustrates a top plan view of the dual port lumen attachment removed from the tamper resistant catheter device of this application.
FIGS. 14A to 14B schematically illustrate a peripherally inserted central catheter or PICC line used in the tamper resistant catheter device of this application, including a top plan view in FIG. 14A and a side view in FIG. 14B.
Figure 15:
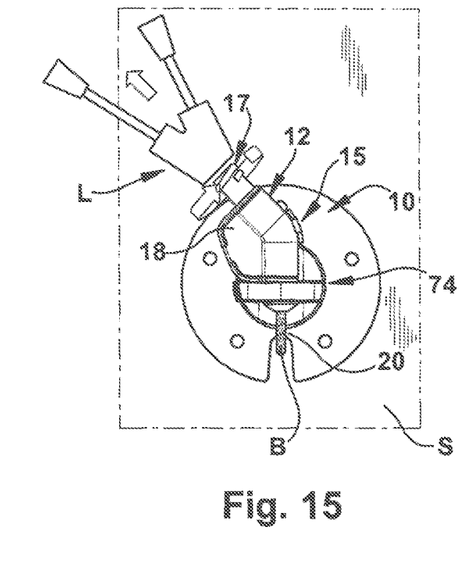
FIG. 15 schematically illustrates removal of the dual port lumen from the lumen adaptor component of the housing, or the reverse process shown in FIG. 6.

To administer authorized medications, a health care provider first attaches a lumen attachment L, shown in FIGS. 6 and 13 as a dual port attachment, using a mating threaded connector to interconnect with the threaded lumen adaptor end 17. Once attached, an authorized medicine M in a vial may be injected into one of the lumen attachment ports, as in FIG. 7. To administer the medicine from the vial, the health care provider opens the line clamp portion 18 at the hinge joint 15, which unclamps the stops 60 from the line 20 and enables medication to flow the patient through the line 20, all as shown in FIG. 8. Once the desired medicine M within the vial has been dispensed, the line clamp portion 18 is closed to clamp the line 20, as shown in FIG. 9. It is understood that the threaded lumen adaptor end 17 of the line retainer 14 may be configured as any suitable fitting, such as either a female Luer or male Luer lock connection, Luer taper (male or female), or the like to receive a fluid source, such as a syringe, with any lumen attachment provided with an appropriate mating connection.

Figure 2:
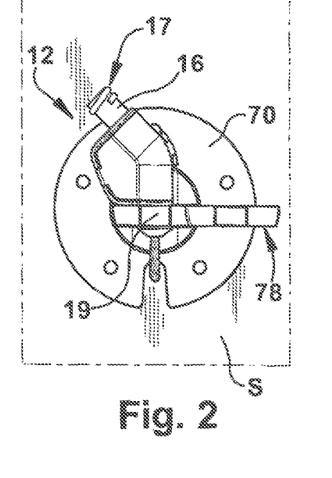
FIG. 2 is a top plan view of the PICC line and housing of FIG. 1, mounted within a line retainer mount, shown in an open position, supported on an adhesive backed support pad.
Figure 3:
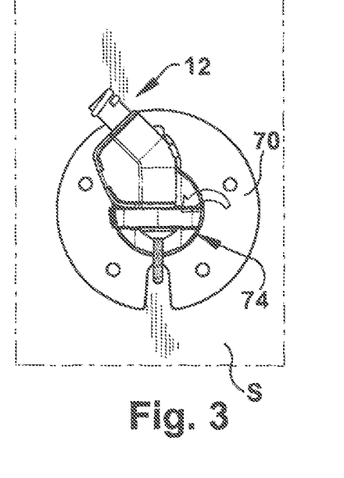
FIG. 3 is a top plan view of the PICC line and housing of FIG. 2, mounted within a line retainer mount, shown in closed position.
Figure 4:
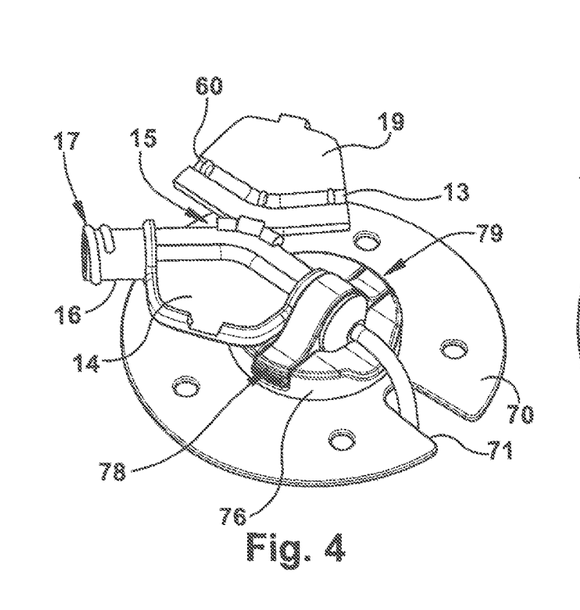
FIG. 4 is a perspective view of the PICC line housing in an open position for viewing the PICC line and internal structure of the hinged line retainer and clamp forming the housing.
Figure 5:
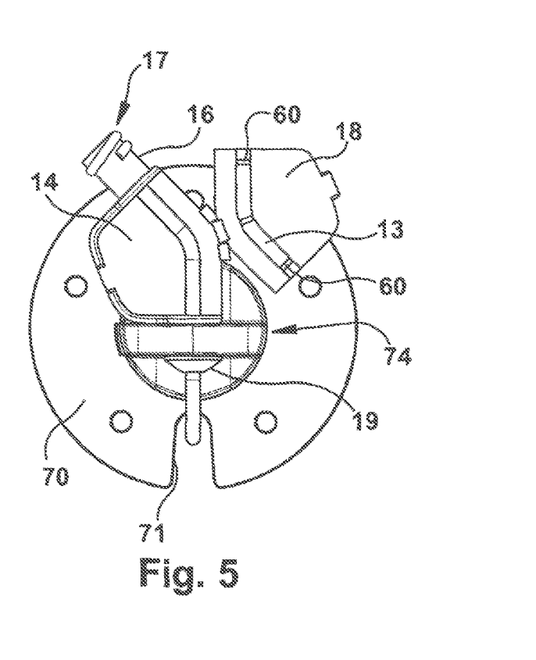
FIG. 5 is a top plan view of the PICC line housing of FIG. 4 in open position for viewing the PICC line and the internal structure of the housing.

To maintain the device 10 during normal wearing, the housing 12 may be secured to the patient's skin S using an adhesive pad 70 with a line retainer mount 74 adhesively secured to the pad, as shown in FIGS. 3 and 4. In FIG. 2, the adhesive backed pad, which supports the line retainer mount, is applied to the patient's skin S. The line retainer mount is shown with a latchable closure portion 78 in open position in FIG. 2. The line retainer end 19 of the base 14 is placed within a channel of the line retainer mount 74, prior to closing and latching the closure portion 78 to retain and support the housing in a secure position. A U-shaped cutout 71 in the pad 70 partially surrounds the line 20 to aid in positioning. The line retainer mount includes a base 76 and the closure portion 78, which is hinged to the base at a joint 79, as shown in FIGS. 2, and 12A to 12C. However, the housing 12 can freely rotate once the line retainer mount is closed.

Following administration of any authorized medications, the lumen attachments are removed, and the device may be locked to prevent unauthorized access to the inlet port 22 of the catheter line 20. To prevent access to the line 20, locking mechanism embodiments are disclosed which address several factors, including securing the inlet port of the catheter line to prevent unauthorized access, deterring patients from tampering, providing a mechanism which is familiar to health care providers for ease of use in a medical setting.

Figure 16:
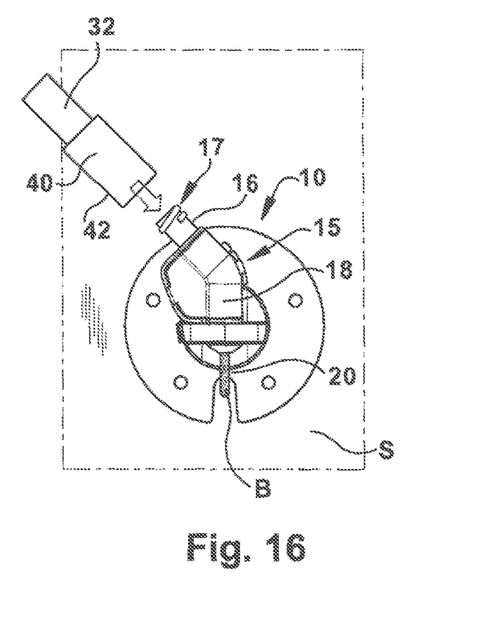
FIG. 16 schematically illustrates installation of the locking or slotted retaining sleeve and threaded cap with installation tool being installed over the lumen adaptor component of the base or line retainer portion of the housing.
Figures 17, 18:
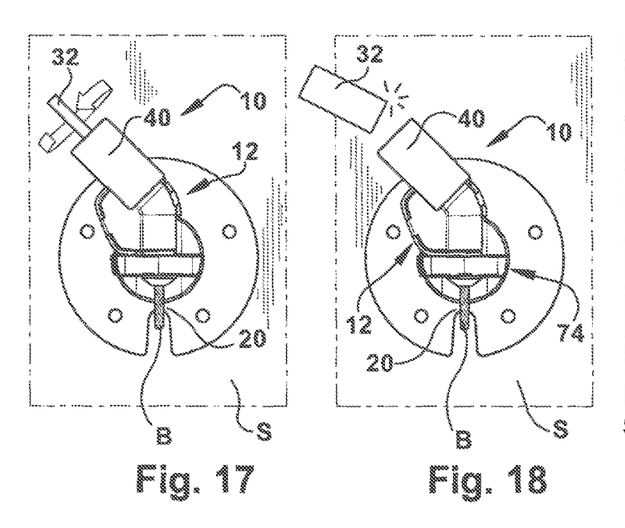
FIG. 17 schematically illustrates locking of the slotted retaining sleeve and threaded cap over the lumen adaptor component by rotating the installation tool portion of the threaded cap to engage and lock the slotted retaining sleeve and threaded cap in threaded engagement with and over the lumen adaptor component.
FIG. 18 schematically illustrates removal of the installation tool component from the threaded cap to secure the threaded cap and slotted retaining sleeve engaged with and covering the lumen adaptor component, base and line clamp portions.

In FIGS. 16 to 20C, a first embodiment of the locking components of the tamper resistant catheter device are illustrated. To secure and maintain the housing 12 in a closed and locked condition, a locking cap or threaded locking cap or internally threaded locking cap 30 (FIG. 20A) and slotted locking or retaining sleeve (FIG. 20B), as well as the stand-alone, separate removal tool 50 (FIG. 20C) are provided. After removal of the lumen attachment L from the lumen adaptor component 16 of the housing 12, the locking cap 30, which is aligned in position partially within the slotted retaining sleeve 40, is placed over the threaded end 17 of the lumen adaptor component 16 of the housing 12, as shown in FIG. 16. The threaded locking cap 30 includes a detachable installation tool or breakaway handle portion 32, which is the portion of the threaded locking cap which is used by the health care provider to hold the threaded locking cap, as it is supported within the slotted retaining sleeve 40 and positioned over the lumen adaptor component. A single slot 42 of the slotted retaining sleeve 40 is aligned to surround the closed components of the base 14 and line clamp portion 18, and enable slidable movement of the sleeve 40 and locking cap 30 over the end of the inlet adaptor to cover, trap and prevent any access to the inlet port of the catheter line. The slotted retaining sleeve is configured with the slot engaging the housing to block catheter access and prevent opening of the housing, providing a "lock out" position. The slotted retaining sleeve 40 shown in the embodiment of FIGS. 16 to 20B is provided with a single slot 42. Other sleeve embodiments having additional slots will be referenced using this same reference numeral, but with a prime designation. While the slotted retaining sleeve 40 and locking cap 30 are positioned as in FIG. 17, the installation tool portion 32 is rotated to engage the internal threads of the locking cap with the threaded end 17 of the lumen adaptor component 16, and to engage locking components on the locking cap 30 with interfitting locking surfaces in the slotted retaining sleeve.

Figure 19A:
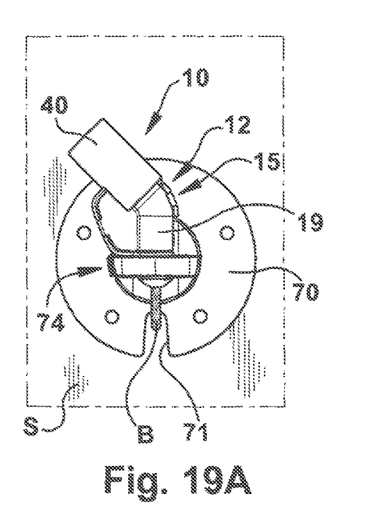
FIGS. 19A and 19B schematically illustrate the tamper resistant catheter device of this application with the slotted retaining sleeve and threaded cap engaged to resist removal from the housing, and prevent access to an open portion of the PICC line, including a top plan view in FIG. 19A and a perspective side view in 19B.
Figure 19B:
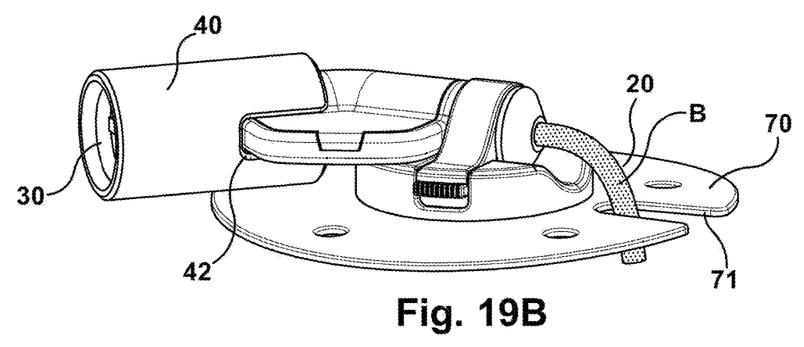
Figure 20A:
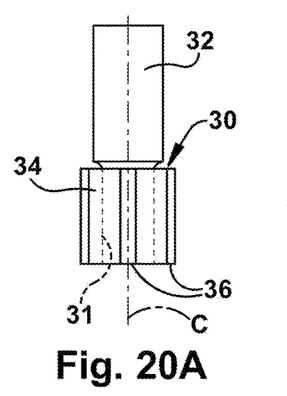
FIGS. 20A to 20C schematically illustrate side views of the threaded cap with installation tool in 20A, the locking or retaining sleeve in 20B and the removal tool in 20C.
Figure 20B:
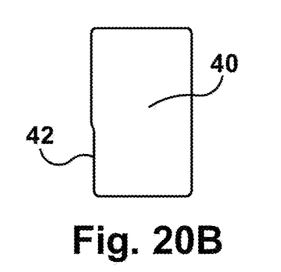
Figure 20C:
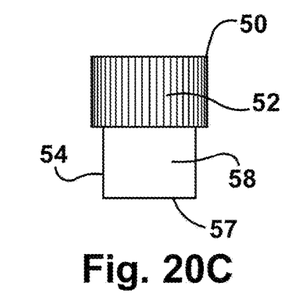

The locking components of the threaded locking cap 30 and slotted retaining sleeve 40 are shown in FIGS. 34A to 35D. The threaded locking cap 30 includes an annular skirt 34 forming the cup-shaped locking cap. The annular skirt 34 is configured with spaced ribs or lugs 36 extending outwardly from the skirt. As shown in FIGS. 34B and 34C, four ribs 36 are provided spaced radially around the skirt, for the full height of the skirt, and are aligned with a central axis C of the locking cap 30. The ribs 36 are cooperating elements with the interfitting locking surfaces 44 on the slotted retaining sleeve 40, which include a similar number of arcing ramps 48 adjacent to and terminating at the locking surfaces 44. The ramps 48 and locking surfaces 44 are spaced radially around and on an inner annular surface 46 of the sleeve, shown in FIGS. 26A and 35A. As the installation tool portion 32 of the cap is rotated, and the threads 31 of the threaded cap 30 and the threaded end 17 of the lumen adaptor component 16 mate and engage, the ribs 36 engage the ramps 48 until they reach the locking surfaces 44, and are then prevented from reverse movement to unthread and remove the threaded cap from the lumen adaptor. The internal shape of the retaining sleeve and locking cap are configured to allow the cap to be turned only in one direction for tightening. By this action, the cap 30 is in threaded engagement with the housing 12 to prevent axial removal of the cap, and the cap is engaged with the sleeve 40 to prevent rotational removal of the cap. The installation tool portion 32 may then be broken or snapped off for disposal, as in FIG. 18, leaving the locking cap 30 secured within the locking sleeve 40 in lock out position. Once the installation tool portion 32 is removed, the tamper resistant catheter device 10 appears with the locking sleeve 40 in part covering or blocking the housing 12 to prevent opening and access to the catheter line 20, as shown in FIGS. 19A-B. The locking cap 30 with installation tool portion 32, slotted retaining or locking sleeve 40 and removal tool 50 components are schematically illustrated in FIGS. 20A-C. Again, it should be understood that the internal threaded configuration of the locking cap may have threads for mating interconnection with whichever commercially available fitting, such as a female Luer or male Luer lock connection, Luer taper (male or female), or the like, is provided in the lumen adaptor end of the line retainer component.

Figure 21:
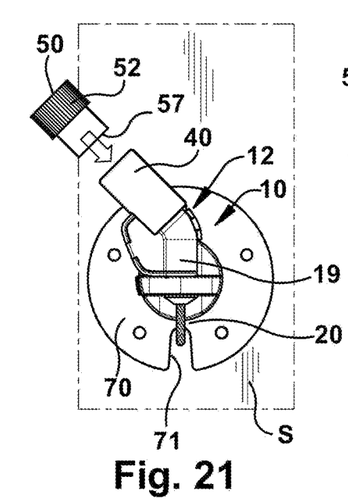
FIG. 21 schematically illustrates installation of the removal tool into the retaining sleeve and threaded cap.
Figure 22:
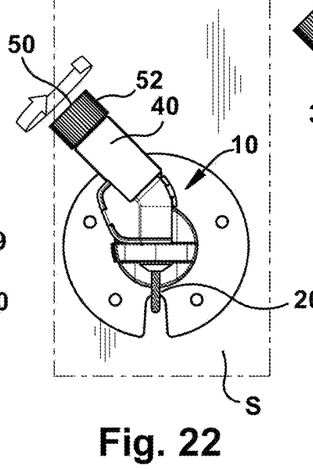
FIG. 22 schematically illustrates rotation of the removal tool engaged with the threaded cap and retaining sleeve to disengage the threaded cap.
Figure 23:
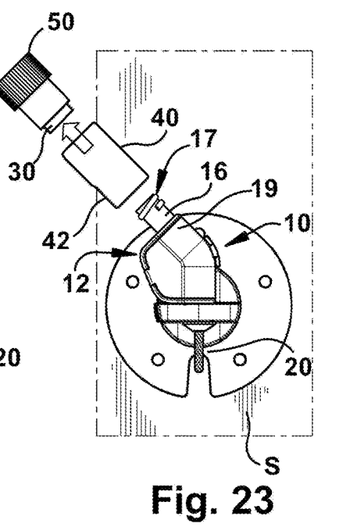
FIG. 23 schematically illustrates removal of the removal tool and threaded cap, and the retaining sleeve, from the lumen adaptor component to allow authorized access to the PICC line.
Figure 24:
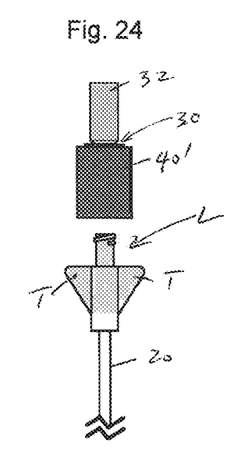
FIG. 24 shows the threaded cap with installation tool engaged with the retaining sleeve and positioned for engagement with the PICC line lumen.
Figures 29, 30, 30A, 31, 34A, 34B, 34C, 35A, 35B, 35C, 35D:
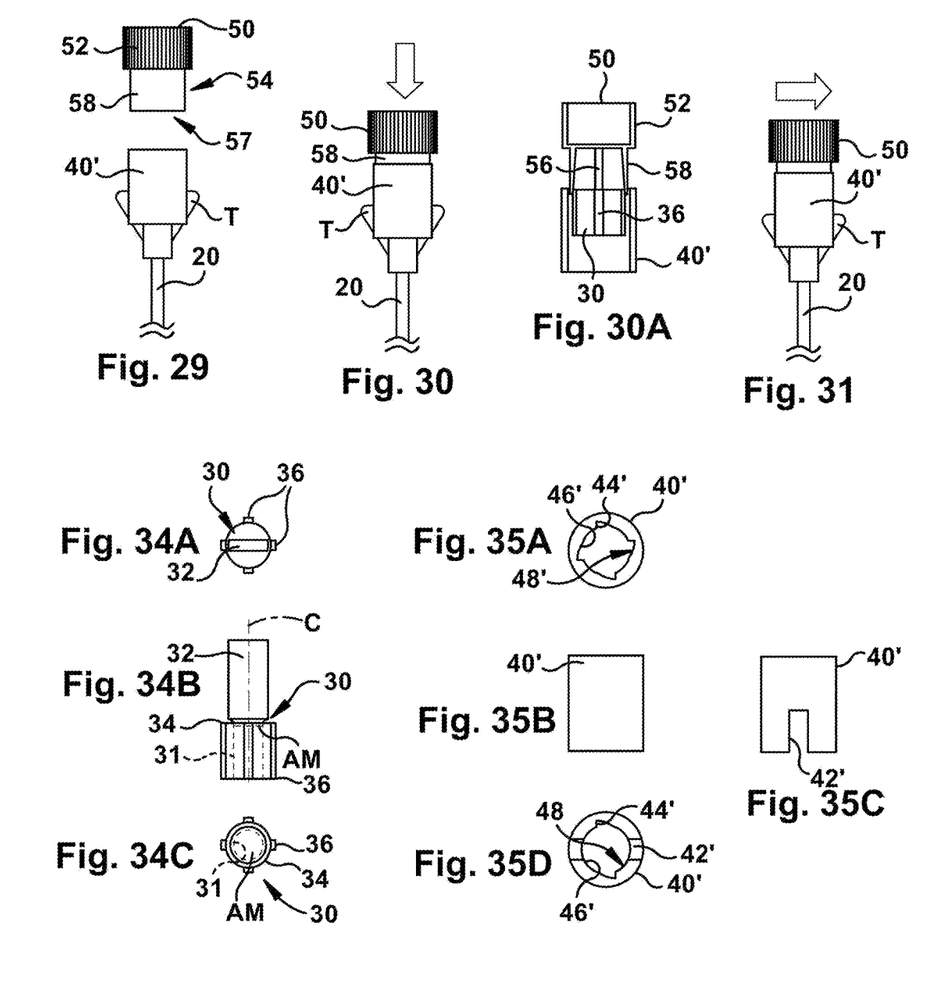
FIG. 29 shows a removal tool positioned prior to engagement with the threaded cap and retaining sleeve.
FIG. 30 schematically illustrates installation and engagement of the removal tool into the threaded cap and retaining sleeve.
FIG. 30A illustrates a cut-away side view of the removal tool aligned for engagement with the threaded cap and retaining sleeve.
FIG. 31 schematically illustrates a side view showing counterclockwise rotation of the engaged removal tool to unlock the threaded cap from the PICC line lumen threads and disengagement of the retaining sleeve.
FIGS. 34A to 34C schematically illustrate various views of the threaded cap and installation tool portion of FIG. 24: a top view of the threaded cap and installation tool portion in FIG. 34A; a side view in FIG. 34B and a bottom view in FIG. 34C.
FIGS. 35A to 35D schematically illustrate various views of the slotted retaining sleeve of FIG. 25A: a top view of the slotted retaining sleeve in FIG. 35A; a front view in FIG. 35B; a side view in FIG. 35C; and a bottom view in FIG. 35D.
Figures 32, 33, 36A, 36B, 36C:
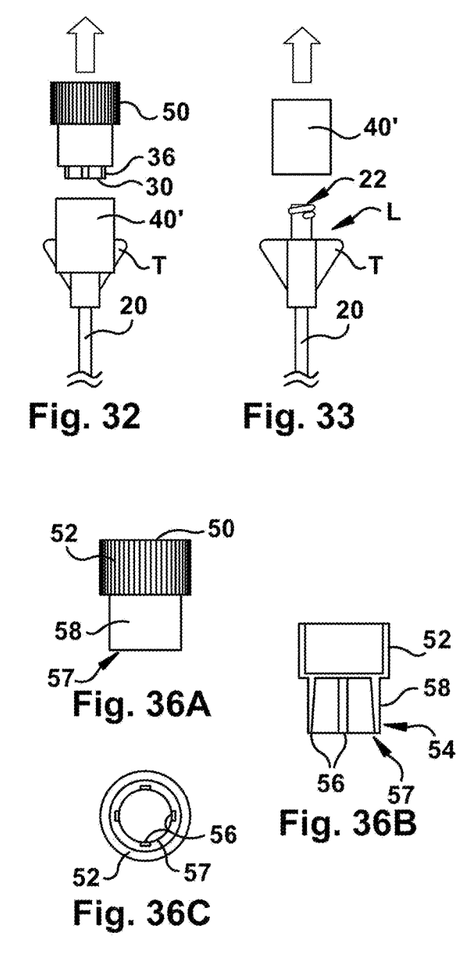
FIG. 32 schematically illustrates removal of the removal tool and threaded cap from the retaining sleeve.
FIG. 33 schematically illustrates removal of the slotted retaining sleeve from the PICC line lumen to allow authorized access to the PICC line.
FIGS. 36A to 36C schematically illustrate various views of the removal tool of FIGS. 20C and 29: a side view of the removal tool in FIG. 36A; a cut-away side view in FIG. 36B; and a bottom view in FIG. 36C.

When a health care provider desires authorized access to a patient's catheter line 20, the removal tool 50 is used to remove the locking cap 30 and slotted retaining sleeve 40. The removal tool in FIGS. 20C, 36A to 36C, includes a finger surface 52 for rotating the tool 50, and an annular skirt 54 having spaced grooves 56 for mating engagement with the spaced ribs 36 in the locking cap 30. When the removal tool grooves 56 are aligned with the locking cap ribs 36, the removal tool is slidably inserted between the threaded cap and the slotted retaining sleeve, as shown in FIGS. 30A and 21. As shown, the grooves 56 have a slight slope or incline, so that the groove is narrower or less deep at the insertion edge 57, and slightly deeper toward the finger surface 52, to assist, as a wedge, with insertion of the removal tool between the locking cap and the slotted retaining sleeve. Thereafter, a health care provider uses the finger surface 52, to rotate the removal tool 50, FIGS. 22 and 31, to disengage the interfitting locking surfaces 44 from the spaced ribs 36 of the locking cap 30, and unthread the locking cap from the lumen adaptor component 16. Thereafter the locking cap 30 is removed with the removal tool 50, as shown in FIGS. 23 and 32, and the retaining sleeve 40 may also be removed. The housing 12 may then be opened for access by authorized health care providers.

Figure 25:
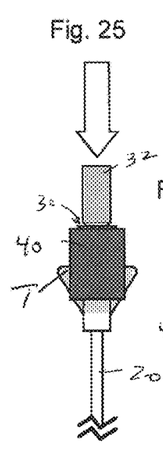
FIG. 25 shows the threaded cap and retaining sleeve engaged with the PICC line lumen.
Figure 25A:
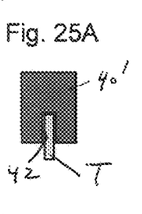
FIG. 25A shows a side view of the threaded cap and retaining sleeve engaged with the PICC line lumen of FIG. 25.
Figures 26, 26A:
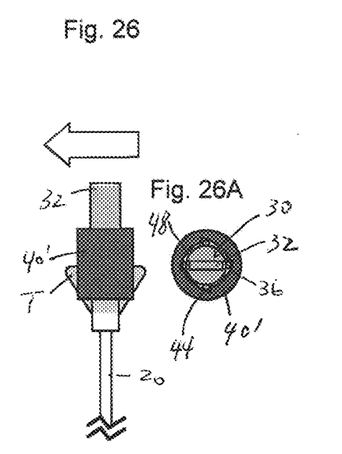
FIG. 26 schematically illustrates clockwise rotation of the installation tool portion of the threaded cap to engage the threads of the threaded cap and the PICC line lumen, and to lock engagement of the threaded cap within the retaining sleeve.
FIG. 26A schematically illustrates a top view of the threaded cap and retaining sleeve of FIG. 26.
Figure 27:
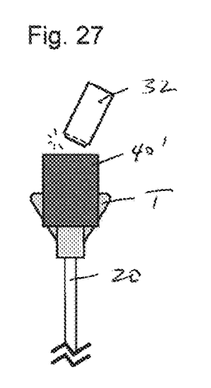
FIG. 27 schematically illustrates removal of the installation tool portion from the threaded cap.
Figure 28:
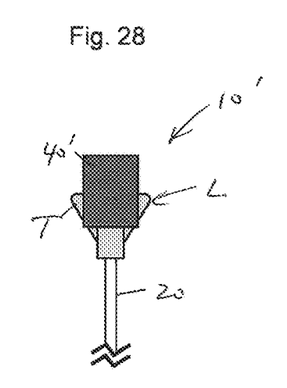
FIG. 28 schematically illustrates the tamper resistant catheter device of this application with the slotted retaining sleeve and threaded cap engaged to resist removal from the PICC line lumen, and prevent access to an open portion of the PICC line.

An alternative lockout device 10' or locking mechanisms for a currently available commercial PICC line 20' manufactured and sold as the Arrow® brand by Teleflex Incorporated of Wayne, Pa., is shown in FIGS. 24 to 28. As the device 10 previously described with respect to FIGS. 1 to 23 is substantially similar, some differences are highlighted further, and a prime designation is used to designate similar structure in this alternate embodiment. As with the first embodiment, the retaining sleeve 40' and threaded cap 30 shown in FIG. 24 may be provided as pre-assembled components, which would be provided to authorized health care providers in a sterile pack. The locking mechanism (retaining sleeve 40' and threaded cap 30) slides down over the Arrow® brand PICC line lumen 20'. The slotted retaining sleeve 40' includes two opposing slots 42', and slides over the lumen tabs T, as shown in FIGS. 25 and 25A. The threaded cap 30 is then tightened by rotating the installation tool portion 32 of the threaded cap, as shown in FIG. 26, where the interfitting locking surfaces 44 and ramps 48 on the inner annular surface 46 of the slotted retaining sleeve 40' are configured to allow the cap to be turned only in a one direction (shown as clockwise) for tightening, as with the first embodiment. Once the cap is tightened, the installation tool component 32 is then broken off, as in FIG. 27, and access to an inlet port within the PICC line 20' is prevented by the threaded locking cap 30 and sleeve 40' that remain, as in FIG. 28.

To remove the locking cap 30 and slotted sleeve 40' from the PICC line 20', the removal tool 50 is required, and is positioned as in FIG. 29. First, the removal tool is inserted into the top of the slotted retaining sleeve 40' and locking cap 30, as in FIG. 30, which drives a wedge between the threaded cap 30 and the retaining sleeve 40' to separate the locking ribs 36 holding the components in position, as shown in the cut-away view in FIG. 30A. With the removal tool 50 in place, the removal tool as in FIG. 31, as the external surface 58 of the removal tool within the retaining sleeve is smooth or unobstructed freely turns the threaded cap 30. The threaded cap is then removed from engagement with the threads of the PICC line 20' lumen, and may be pulled out by sliding out the removal tool, as in FIG. 32. The slotted retaining sleeve 40' is then removed, as in FIG. 33, for authorized access to the PICC line 20'.

The three components of the tamper resistant catheter device for use with the Arrow® brand PICC line lock out embodiment are set forth in top, bottom and side views in FIGS. 34A to 36C, where FIGS. 34A to 34C show the threaded cap 30, FIGS. 35A to 35D show the two slotted retaining sleeve 40' and FIGS. 36A to 36C show the removal tool 50. The various components of the tamper resistant catheter device 10, 10' may be made from any suitable material capable of appropriate medical sterilization. Examples of suitable materials include plastics or other polymers, resins, metals or the like. In particular, the locking components may be made from a plastic such as nylon or other thermoplastic. The components may be formed in any suitable manner. Examples of suitable forming methods may include, for example, injection molding, molding, 3D printing, milling, or the like.

It should be understood that color-coding of the locking caps (red), locking sleeves (blue) and removal tools (green) to accomplish ease of use may be included with the catheter locking devices disclosed here. In addition to the above mentioned tamper resistant catheter or PICC line lock out devices, additional benefits to include with lock out devices include providing an anti-microbial layer AM or coating of material on an inside surface or surfaces of the locking cap, in order to treat the threaded end of the lumen adaptor component adjacent the inlet port of the catheter line for reducing infection.

It should be further understood that the tamper resistant catheter device is not limited to the particular construction and arrangement of parts illustrated and described here, but embraces all such modified forms as come within the scope of the following claims.

We claim:

1. A tamper resistant catheter device for resisting unauthorized intravenous administration of substances to a patient comprising,
    a catheter line having an inlet port;
    a catheter line retainer having a base for supporting the catheter line, a threaded lumen adaptor adjacent the inlet port of the catheter line, and a line clamp for covering and trapping the catheter line within the catheter line retainer, and the line clamp having stops for engaging and clamping the catheter line within the catheter line retainer to prevent flow through the catheter line;
    a threaded locking cap for threaded engagement covering the threaded lumen adaptor, and having external rib portions;
    a slotted retaining sleeve having interfitting locking surfaces for engaging the external rib portions of the threaded locking cap, and where the slotted retaining sleeve and threaded locking cap are interconnected and are installed for engagement of the threaded locking cap surrounding the threaded lumen adaptor, and the slotted retaining sleeve is engaged surrounding the base and line clamp for resisting unauthorized access to the inlet port of the catheter line, and
    a removal tool configured to disengage the interfitting locking surfaces of the slotted retaining sleeve from the external rib portions of the threaded locking cap.

2. The tamper resistant catheter device of claim 1, wherein the threaded locking cap further comprises an interconnected handle portion, configured to install the threaded locking cap and slotted retaining sleeve surrounding the base and line clamp, and the interconnected handle portion is configured to be removed or broken away from the threaded locking cap following installation.

3. The tamper resistant catheter device of claim 1, wherein the interfitting locking surfaces of the slotted retaining sleeve comprise arcing ramp surfaces, each terminating at an interfitting locking surface configured to engage an external rib portion of the threaded locking cap when installed over the threaded lumen adaptor, and to prevent reverse rotation and removal of the threaded locking cap from disengagement with the threaded lumen adaptor without the use of the removal tool.

4. The tamper resistant catheter device of claim 3, wherein the slotted retaining sleeve has a single slot formed in a side wall of the sleeve for engagement surrounding the catheter line retainer.

5. The tamper resistant catheter device of claim 3, wherein the removal tool includes a handle portion and an annular skirt provided with internal grooves for mating engagement with the external rib portions.

6. The tamper resistant catheter device of claim 1, wherein an inside surface of the threaded locking cap for engagement with the lumen adaptor includes a coating of anti-microbial material.

7. A catheter line lock comprising,
    an internally threaded locking cap, a lumen adaptor, an inlet port to a catheter line, and a catheter line, wherein the internally threaded locking cap is rotatable into threaded engagement with the lumen adaptor adjacent the inlet port to the catheter line, the internally threaded locking cap having an installation portion comprising a breakaway handle, and an annular skirt with outwardly extending ribs; and
    a slotted retaining sleeve having interfitting locking surfaces for engagement with the outwardly extending ribs of the internally threaded locking cap to secure the internally threaded locking cap in threaded engagement with the lumen adaptor, prevent removal of the internally threaded locking cap, and prevent unauthorized access to the inlet port of the catheter line.

8. The catheter line lock of claim 7 further comprising a removal tool for disengaging the internally threaded locking cap and slotted retaining sleeve from the lumen adaptor.

9. The catheter line lock of claim 8, wherein the removal tool includes a handle portion and an annular skirt configured for engagement intermediate a side wall of the slotted retaining sleeve and the outwardly extending ribs of the threaded locking cap, and the annular skirt of the removal tool is provided with internal grooves for mating and sliding axial engagement along the outwardly extending ribs.

10. The catheter line lock of claim 7, wherein the breakaway handle of the installation portion is configured to be removed from the internally threaded locking cap following installation of the slotted retaining sleeve and internally threaded locking cap over the lumen adaptor.

11. The catheter line lock of claim 10, wherein the slotted retaining sleeve includes a side wall configured with two opposite slots for engagement over and surrounding the lumen adaptor.

12. The catheter line lock of claim 7, wherein the interfitting locking surfaces of the slotted retaining sleeve comprise arcing ramp surfaces in an end of the sleeve, each arcing ramp surface terminating at an interfitting locking surface configured to engage an outwardly extending rib of the internally threaded locking cap when installed over the lumen adaptor, and to prevent reverse rotation and removal of the internally threaded locking cap from disengagement with the lumen adaptor.

13. The catheter line lock of claim 7, wherein an inside surface of the threaded locking cap for engagement with the lumen adaptor includes a coating of anti-microbial material.

14. The catheter line lock of claim 7, wherein the catheter line is configured as any line or tube having an inlet port used to supply medications to a patient.

* * * * *